(12) United States Patent
Thompson et al.

(10) Patent No.: US 10,198,555 B2
(45) Date of Patent: Feb. 5, 2019

(54) METHOD AND APPARATUS FOR IMPLEMENTING PATIENT DATA DOWNLOAD FOR MULTIPLE DIFFERENT METER TYPES

(75) Inventors: Brian C. Thompson, Osceola, IN (US); Joseph E. Ruggiero, Goshen, IN (US); Richard A. Lett, Spring Grove, IL (US)

(73) Assignee: Ascensia Diabetes Care Holdings AG, Basel (CH)

( * ) Notice: Subject to any disclaimer, the term of this patent is extended or adjusted under 35 U.S.C. 154(b) by 2181 days.

(21) Appl. No.: 11/579,556

(22) PCT Filed: May 13, 2005

(86) PCT No.: PCT/US2005/016570
§ 371 (c)(1),
(2), (4) Date: Aug. 30, 2007

(87) PCT Pub. No.: WO2005/114534
PCT Pub. Date: Dec. 1, 2005

(65) Prior Publication Data
US 2008/0109259 A1    May 8, 2008

Related U.S. Application Data

(60) Provisional application No. 60/571,390, filed on May 14, 2004.

(51) Int. Cl.
*G06Q 50/00* (2012.01)
*G06F 19/00* (2018.01)
(Continued)

(52) U.S. Cl.
CPC ...... *G06F 19/3418* (2013.01); *A61B 5/14532* (2013.01); *G06F 19/00* (2013.01);
(Continued)

(58) Field of Classification Search
CPC . C12Q 1/006; G06F 19/3418; G06F 13/4068; Y02W 90/20; G01N 33/48785;
(Continued)

(56) References Cited

U.S. PATENT DOCUMENTS

| 4,695,955 A | 9/1987 | Faisandier |
| 5,251,126 A * | 10/1993 | Kahn et al. ............... 600/309 |

(Continued)

FOREIGN PATENT DOCUMENTS

| CA | 2472403 A1 | 12/2004 |
| WO | WO 98/29790 A | 7/1998 |

OTHER PUBLICATIONS

Search Report for PCT/US2005/016570 which claims priority to U.S. Appl. No. 60/571,390 (dated Mar. 15, 2006).
(Continued)

*Primary Examiner* — Victoria P Shumate
*Assistant Examiner* — Teresa S Williams
(74) *Attorney, Agent, or Firm* — Nixon Peabody LLP

(57) ABSTRACT

A method and apparatus implements patient data downloading for multiple different meter types, such as multiple different blood glucose meters. A plurality of serial ports is provided, each arranged for connection to a respective meter of the multiple different meter types. Information is displayed and user selections are identified. Responsive to user entry identifying a particular meter type, a connection port/cable number for the meter connection is displayed for viewing by the user. Predefined instructions for the particular meter type are displayed. A data collection computer system is provided as an integral unit including a unitary housing containing a processor device, a printer, and a display touch screen. When a meter connection is identified, information is displayed, patient data is downloaded from
(Continued)

the meter and is printed in a selected format together with selected reports generated from the downloaded patient data.

21 Claims, 3 Drawing Sheets

(51) Int. Cl.
*A61B 5/145* (2006.01)
*G06Q 50/22* (2018.01)
*G06Q 50/24* (2012.01)
*G16H 40/63* (2018.01)

(52) U.S. Cl.
CPC ............. *G06Q 50/22* (2013.01); *G06Q 50/24* (2013.01); *G16H 40/63* (2018.01); *A61B 2560/0443* (2013.01)

(58) Field of Classification Search
CPC ............ G01N 35/0087; H02J 2007/005; H02J 2007/0098; H02J 7/0047; A61B 5/14532; A61B 5/14546
USPC ............ 705/2, 3; 600/309, 300–301; 435/25
See application file for complete search history.

(56) References Cited

U.S. PATENT DOCUMENTS

| | | | |
|---|---|---|---|
| 5,371,687 A * | 12/1994 | Holmes et al. ................. 710/72 |
| 5,379,214 A * | 1/1995 | Arbuckle et al. ............. 600/301 |
| 5,594,906 A * | 1/1997 | Holmes et al. ............... 713/300 |
| 5,781,442 A * | 7/1998 | Engleson et al. ............. 700/214 |
| 6,101,478 A * | 8/2000 | Brown ............................... 705/2 |
| 6,175,752 B1 * | 1/2001 | Say ..................... A61M 5/1723 128/903 |
| 6,336,900 B1 * | 1/2002 | Alleckson et al. ........... 600/485 |
| 6,368,272 B1 * | 4/2002 | Porumbescu ................. 600/300 |
| 6,403,897 B1 * | 6/2002 | Bluth ................... A61B 5/0002 128/920 |
| 6,428,124 B1 * | 8/2002 | Bluth et al. ................... 312/194 |
| 6,493,568 B1 | 12/2002 | Bell et al. |
| 6,602,191 B2 * | 8/2003 | Quy ............................... 600/300 |
| 6,692,436 B1 * | 2/2004 | Bluth et al. ................... 600/300 |
| 6,740,059 B2 * | 5/2004 | Flaherty .......................... 604/67 |
| 6,975,892 B2 * | 12/2005 | Burd .................. A61B 5/14532 600/316 |
| 7,241,265 B2 * | 7/2007 | Cummings et al. .......... 600/300 |
| 7,285,090 B2 * | 10/2007 | Stivoric et al. ............... 600/300 |
| 7,399,276 B1 * | 7/2008 | Brown et al. ................. 600/300 |
| 7,537,571 B2 * | 5/2009 | Freeman .............. A61B 5/1411 600/583 |
| 7,647,237 B2 * | 1/2010 | Malave et al. ..................... 705/3 |
| 8,612,159 B2 * | 12/2013 | Say et al. ......................... 702/19 |
| 8,672,844 B2 * | 3/2014 | Say et al. ....................... 600/365 |
| 2002/0077856 A1 | 6/2002 | Pawlikowski et al. |
| 2002/0193679 A1 * | 12/2002 | Malave ................. A61M 5/172 600/407 |
| 2003/0050538 A1 * | 3/2003 | Naghavi ............... G06F 19/322 600/300 |
| 2003/0141840 A1 * | 7/2003 | Sanders ................ H02J 7/0042 320/107 |
| 2003/0199739 A1 * | 10/2003 | Gordon ............... G06F 19/3406 600/300 |
| 2003/0211782 A1 | 11/2003 | Esparaz et al. |
| 2004/0032426 A1 | 2/2004 | Rutledge et al. ............. 345/764 |
| 2004/0073464 A1 * | 4/2004 | Huang ................. A61B 5/0002 705/3 |
| 2004/0093167 A1 * | 5/2004 | Braig ................... A61B 5/0002 702/23 |
| 2005/0038680 A1 | 2/2005 | McMahon |
| 2005/0192841 A1 * | 9/2005 | Hays et al. ........................ 705/2 |
| 2005/0214892 A1 * | 9/2005 | Kovatchev et al. ............ 435/25 |
| 2005/0228245 A1 * | 10/2005 | Quy ...................... A61B 5/1112 600/301 |
| 2009/0275809 A1 * | 11/2009 | Starr ............................. 600/301 |

OTHER PUBLICATIONS

Written Opinion for PCT/US2005/016570 which claims priority to U.S. Appl. No. 60/571,390 (dated Mar. 15, 2006).

* cited by examiner

METHOD AND APPARATUS FOR IMPLEMENTING PATIENT DATA DOWNLOAD FOR MULTIPLE DIFFERENT METER TYPES

CROSS-REFERENCE TO RELATED APPLICATION

This application claims priority to Application No. 60/571,390 filed on May 14, 2004, which is incorporated by reference in its entirety.

FIELD OF THE INVENTION

The present invention relates generally to blood glucose meters, and more particularly, relates to a method and apparatus for implementing patient data download for multiple different meter types, such as multiple different types of blood glucose meters.

DESCRIPTION OF THE RELATED ART

The quantitative determination of analytes in body fluids is of great importance in the diagnoses and maintenance of certain physiological abnormalities. For example lactate, cholesterol and bilirubin should be monitored in certain individuals. In particular, the determination of glucose in body fluids is of great importance to diabetic individuals who must frequently check the level of glucose in their body fluids as a means of regulating the glucose intake in their diets. While the remainder of the disclosure herein will be directed towards the determination of glucose, it is to be understood that the procedure and apparatus of this invention can be used with other diagnostic systems.

Home glucose monitoring by diabetics is becoming increasingly routine in modern-day diabetes management. Historically patients were required to maintain hand-written paper log books for manually recording glucose readings and other relevant information. More specifically, patients measured their blood glucose at scheduled times, and recorded this information in a personal log book.

Known diagnostic systems, such as, blood glucose systems include a biosensor used to calculate the actual glucose value based on a measured output and the known reactivity of the reagent sensing element used to perform the test. The test results typically are displayed to the user and stored in a memory in the blood glucose meter. In some known systems, the multiple stored values from the blood glucose meter are periodically transferred to a separate computer, for example to enable analysis by a doctor for the blood glucose monitor user.

While the introduction of glucose meters with various memory functions has greatly simplified the data recording process and increased the reliability of stored data, the large amounts of recorded data have made the interpretation task complicated. It is also possible with present-day devices for patients to record other clinically relevant data such as diet and exercise factors, and life-style information. All such stored data can conveniently be transferred to a physician's office, typically via a communications link such as a direct meter cable connection or an acoustic modem line, where it can be reviewed in printed or displayed form for making appropriate treatment recommendations.

Many traditional approaches to automated analysis of diabetes data provide a relatively superficial analysis and an assortment of graphical displays based upon certain predefined statistical calculations. However, the time-consuming and complicated synthesis and interpretation of clinical implications associated with the processed data still need to be performed by the reviewing physician, and significant interaction is still required on behalf of the physician.

U.S. Pat. No. 5,251,126 issued Oct. 5, 1993 to Kahn et al., and assigned to the present assignee discloses an automated diabetes data interpretation method referred to as the "IDDI" system, that combines symbolic and numeric computing approaches in order to identify and highlight key clinical findings in the patient's self-recorded diabetes data. The patient data, including blood glucose levels and insulin dosage levels, recorded by a diabetic patient over a period of time by means of a glucose meter or the like, is initially downloaded into a central processing system such as a personal computer. The accepted diabetes data is processed to (a) identify insulin dosage regimens corresponding to predefined significant changes in insulin dosage that are found to be sustained for at least a predefined segment of the overall data collection period, (b) identify statistically significant changes in blood glucose levels resulting across adjacent ones of the identified insulin regimen periods, and (c) identify clinically significant changes in blood glucose levels from within the identified statistically significant glucose level changes. The results of the diabetes data processing are generated in the form of a comprehensive yet easily understandable data interpretation report highlighting the processing results, including details pertaining to the identified insulin regimens and the associated clinically significant changes in glucose levels.

Multiple commercially available clinical analyzers are available for patient use. Due to differences between various commercially available clinical analyzers, a health care professional (HCP) must have compatible software to run, or may require the patient to be present in the HCP's office if the patient does not have the same or similar program at home. The HCP must run the program, switch cables to match the meter, and maintain both hardware and software. Such chores tend to be time consuming and inefficient.

Currently there are many software applications that are available to download stored patient data from blood glucose meters. Most support one brand of meter using one cable. A few support multiple brands of blood glucose meters using multiple cables, but only one serial port. This subsequently requires a switch box device to use the one serial port to connect to several different cables.

A need exists for an improved method and apparatus for implementing data management including patient data download for multiple different meter types, such as multiple different types of blood glucose meters, to aid analysis and treatment by the patient's doctor or HCP and to minimize time required, for example, in running software, switching cables, and downloading stored meter data.

SUMMARY OF THE INVENTION

Important aspects of the present invention are to provide a new and improved method and apparatus for implementing patient data download for multiple different meter types, such as multiple different types of blood glucose meters to aid analysis and treatment; to provide such method and apparatus that eliminates or minimizes the need for user interaction; and to provide such method and apparatus that overcome some disadvantages of prior art arrangements.

In brief, a method and apparatus are provided for implementing patient data download for multiple different meter types, such as multiple different types of blood glucose meters. A plurality of serial ports is provided, with each respective serial port adapted for connection to a respective meter of the multiple different meter types. Information is displayed and user selections are identified. Responsive to user entry identifying a particular meter type, a connection port/cable number for the meter connection is displayed for viewing by the user. Predefined instructions for the particular meter type are displayed.

In accordance with features of the invention, a data collection computer system is provided as an integral unit including a unitary housing containing a processor device, a printer, and a display touch screen. When a meter connection is identified, information is displayed for the user, patient data is downloaded from the meter to the data collection computer system and is printed in a selected format together with selected reports generated from the downloaded patient data.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

In accordance with features of the invention, apparatus or a data collection computer system of the preferred embodiment is provided in the form of a small kiosk with a touch screen, multiple serial ports, each with a respective associated cable, for example, one for each selected brand of blood glucose meter, a CPU, and a printer. A patient using one of the selected brands of blood glucose meters may use the display touch screen to obtain instructions and attach their meter to the specific cable and to obtain a printout of data that is contained in the blood glucose meter. A patient may also use the touch screen to learn how to use several different blood glucose meters.

Figure 1A:
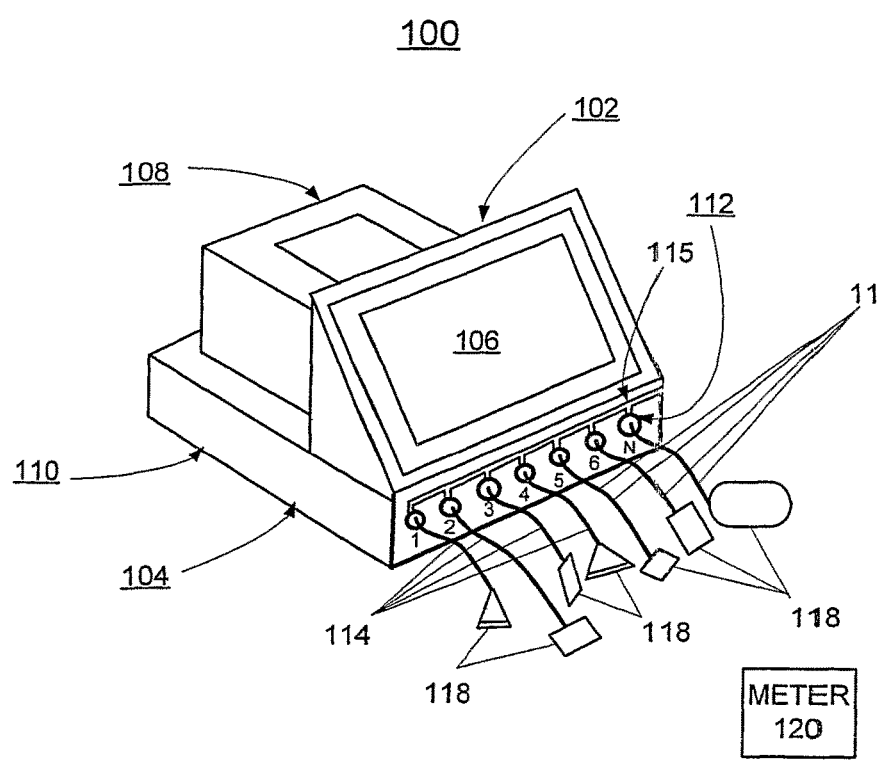
FIG. 1A illustrates an exemplary data collection computer system for implementing patient data download for multiple different meter types in accordance with the present invention.
Figure 1B:
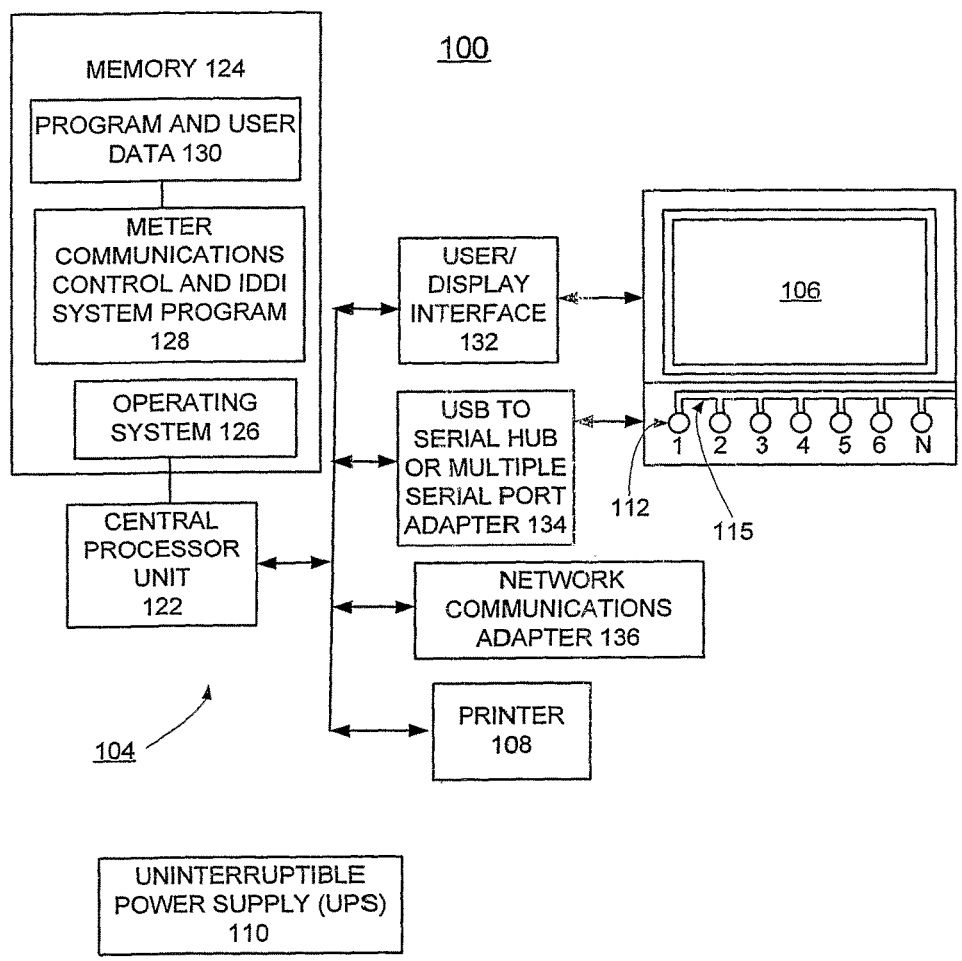
FIG. 1B is a logical block diagram representation of the data collection computer system of FIG. 1A for implementing patient data download for multiple different meter types a in accordance with the present invention.

Having reference now to the drawings, in FIGS. 1A and 1B, there is illustrated an exemplary data collection computer system designated as a whole by the reference character 100 for implementing patient data download for multiple different meter types and arranged in accordance with principles of the present invention. Data collection computer system 100 includes a housing generally designated by reference character 102 containing a computer 104, a display touch screen 106, a printer 108, and an optional uninterruptible power supply 110. Data collection computer system 100 is a unitary system typically located in an office of a health care professional (HCP). Data collection computer system 100 is arranged for use by patients without requiring assistance from any HCP.

In accordance with features of the invention, the data collection computer system 100 eliminates the use of a meter cable switch box. The data collection computer system 100 includes multiple serial ports, one for each brand name and cable type for a particular meter. The user does not need to use a switch box, nor do they have to content with a mass of cables because the cables are contained within the housing 102 and a particular cable type for a particular meter is easily selected. The display touch screen 106 allows the user to interact with the software even when the user is not computer literate. The data collection computer system 100 is arranged to be usable by anyone that can read. The data collection computer system 100 also allows physicians to unburden their offices of the task of downloading blood glucose meters by enabling the patients to do it themselves. The physicians can add new cables as needed, the data collection computer system 100 allows for plugging in of cables by a user and hiding of these cables by the user as well. The data collection computer system 100 also allows for educational materials to be viewed by the patients, thus unburdening the physicians and nursing staff as well.

As shown, data collection computer system 100 includes a plurality of ports 1-N, 112, each for receiving a respective cable 114. An elongated channel 115 is coupled to each of the plurality of ports 1-N, 112 for receiving a respective cable 114. An associated connector 118 is provided with each of the plurality of cable 1-N, 114 for electrically connecting with a particular meter 120. Each of the multiple connectors 118 is arranged for use with a particular one of multiple meter types. The elongated channel 115 is provided for hiding excess cabling within the unitary housing 102 and to enable connection of each of the multiple connectors 118 on the side of the housing.

The meter 120, such as a biosensor or glucose meter 120, is used by the patient and periodically receives and processes a user sample from the patient, then stores or records the measured blood glucose (BG) levels. The patient attaches the meter 120 to its specific cable 1-N, 114 via the associated connector 118 mating with the meter. Some blood glucose meters 120 must be turned on in order to communicate with the data collection computer system 100.

Referring also to FIG. 1B, computer 104 includes a central processor unit (CPU) 122 together with an associated memory 124. Computer 104 includes an operating system 126, a meter communications control and IDDI system program 128 of the preferred embodiment, and program and user data 130 of the preferred embodiment resident in memory 124. Computer 104 includes a user/display interface 132 that couples the display touch screen 106 to the CPU 122, and a USB to serial hub or multiple serial port adapter 134 that couples an attached meter 120 to the CPU 122. Computer 104 includes a network communications adapter 136 for connection, for example, to another computer (not shown) in the doctor's office.

Data collection computer system 100 is shown in simplified form sufficient for understanding the present invention. The illustrated computer test system 100 is not intended to imply architectural or functional limitations. The present invention can be used with various hardware implementations and systems and various other internal hardware devices.

The meter communications control and IDDI system program 128 directs the data collection computer system 100, responsive to a user request for instructions entered via the display touch screen 106, to provide instructions to attach their meter to the specific cable 114 via connector 118 in accordance with the preferred embodiment. The meter communications control and IDDI system program 128 directs the data collection computer system 100 to identify an attached meter 120 and to download patient data and print patient data and reports. The meter communications control and IDDI system program 128 includes the automated intelligent diabetes data interpretation (IDDI) software functions necessary to process, analyze and interpret the self-recorded diabetes patient data and generate selected reports.

U.S. Pat. No. 5,251,126 issued Oct. 5, 1993 to Kahn et al., and assigned to the present assignee, discloses an IDDI system that advantageously included in the IDDI software functions of the meter communications control and IDDI system program 128 in the data collection computer system 100. The subject matter of the above-identified U.S. Pat. No. 5,251,126 is incorporated herein by reference.

Figure 2:
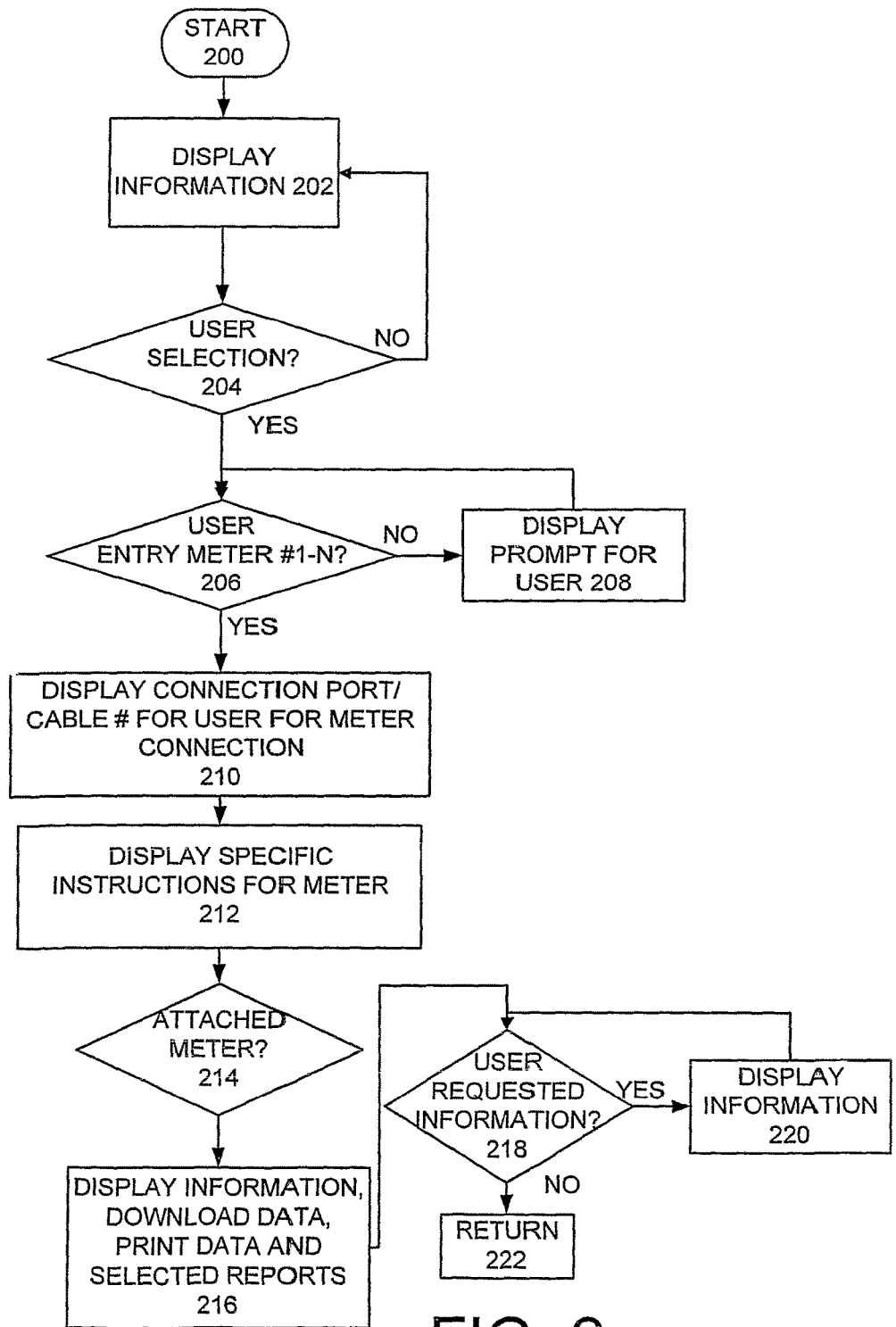
FIG. 2 is a flow chart illustrating exemplary steps performed by the data collection computer system of FIGS. 1A and 1B for implementing patient data download methods in accordance with the present invention.

Referring now to FIG. 2, there are shown exemplary steps performed by the computer system 100 of FIGS. 1A and 1B for implementing patient data download methods in accordance with the present invention starting at a block 200. Information, such as instructions for use of the data collection computer system 100 for viewing by a patient is displayed as indicated in a block 202. Checking for a user selection is performed as indicated in a decision block 204. When a user selection is identified, checking is performed for a user entry identifying a particular meter 120 of the multiple different meter types #1-N as indicated in a decision block 206. When a user entry identifying a particular meter 120 is not identified, a prompt for the user is displayed as indicated in a block 208.

When a user entry identifying a particular meter 120 is identified, a connection port/cable number 1-N for the user is displayed as indicated in a block 210. Specific instructions for the particular meter are displayed as indicated in a block 212. Checking for an attached meter is performed as indicated in a decision block 214. When an attached meter is identified, information for the user is displayed, patient data is downloaded and printed in a selected format together with predefined reports generated from the patient data as indicated in a block 216. Checking for user requested information is performed as indicated in a decision block 218. When user requested information is identified, then information responsive to the user request and predefined educational informational material for viewing by a patient is displayed as indicated in a block 220. When user requested information is not identified, then the exemplary steps return as indicated in a decision block 222.

In accordance with features of the invention, the data collection computer system 100 is a unique product, which naturally combines many creative features into a single coherent unit. The data collection computer system 100 provides significant benefit to the users, both diabetes patients and health care providers, in many ways. For example, the data collection computer system 100 provides great ease of use, one system for all major meters, and timesavings for the health care provider, and eliminates hassle with cables or switch boxes. In brief, the data collection computer system 100 is a new, improved, and effective tool for downloading patient data.

While the present invention has been described with reference to the details of the embodiments of the invention shown in the drawing, these details are not intended to limit the scope of the invention as claimed in the appended claims.

What is claimed is:

1. A data collection kiosk downloading and processing patient analyte data for diagnosing or managing of one or more physiological abnormalities, the data collection kiosk comprising:

a processor device;

a plurality of ports coupled to said processor device, said plurality of ports connecting said processor device with multiple different meter types, each of the respective ports including a respective distinct cable, each respective distinct cable having an associated connector which connects to a respective one of said different meter types, said meter types all being configured to measure patient analyte data and transmit said patient analyte data to said processor device of said data collection kiosk via said cables, said patient analyte data including a determination of analytes in body fluids for diagnosis and maintenance of the one or more physiological abnormalities, said determination of analytes in body fluids including periodical receipt and processing of a fluid sample from the user;

an input device coupled to said processor device and operable for receiving entries from a user;

a display touch screen coupled to said processor device and operable for displaying information and options available for selection by the user, the information and options facilitating the downloading of the patient analyte data via direct interaction between the user and the data collection kiosk without requiring assistance from a health care professional, and a unitary housing containing the processor device, the plurality of ports, the input device, and the display touch screen to form a unitary system for the multiple different meter types, wherein said processor device, responsive to an entry received by said input device from the user identifying one of said meter types, directs the display touch screen to:

display connection information to said user detailing how to connect a meter of the identified meter type to the respective port via said respective distinct cable, and display to said user distinct predefined instructions detailing how to transfer said patient analyte data from the identified meter type to said data collection kiosk, wherein said processor device, responsive to said user fulfilling said predefined instructions, transfers said patient analyte data from the identified meter type to said data collection kiosk without any interaction required from the health care professional, and wherein said processor device, responsive to said transfer of said patient analyte data, presents processed data of at least some of the patient analyte data to the health care professional for synthesis and interpretation of clinical implications.

2. The data collection kiosk of claim 1, further including a printer coupled to said processor device and contained within said unitary housing, said printer being configured for printing downloaded patient data from an attached meter.

3. The data collection kiosk of claim 2, further including a memory coupled to said processor device, said memory storing a meter communications control and intelligent diabetes data interpretation (IDDI) system program, wherein said meter communications control and intelligent diabetes data interpretation (IDDI) system program are configured for generating and printing a selected report from the patient data.

4. The data collection kiosk of claim 2, further including an uninterruptible power supply coupled to said processor device and said printer, said uninterruptible power supply being contained within said unitary housing.

5. The data collection kiosk of claim 2, wherein each of said cables includes an associated connector, each of said associated connectors being configured to connect to a respective one of said different meter types.

6. The data collection kiosk of claim 5, wherein said unitary housing includes a channel connected to each of said plurality of ports, said channel adapted to receive each of said respective cables, said associated connector being arranged for connection to a respective meter without opening said unitary housing.

7. The data collection kiosk of claim 1, further including one of a USB to hub or a multiple port adapter for coupling an attached meter to said processor device.

8. The data collection kiosk of claim 1, wherein said processor device is further programmed to direct the display touch screen to display predefined information for each particular meter type responsive to a user entry.

9. The data collection kiosk of claim 1, wherein said processor device is further programmed to direct the display touch screen to display predefined educational information for viewing by a patient.

10. The data collection kiosk of claim 1, wherein said multiple different meter types all measure a blood glucose level, and each respective meter corresponding to said respective one of said meter types is a blood glucose monitor.

11. The data collection kiosk of claim 1, wherein said multiple different meter types correspond to more than one brand for a meter.

12. A kiosk dedicated to managing data generated by various distinct types of analyte testing meters, the kiosk downloading and processing patient analyte data for diagnosing or managing of one or more physiological abnormalities, the kiosk comprising:
 a unitary housing;
 a central processing unit (CPU) inside the unitary housing;
 an electronic display device mounted to the housing and coupled to the CPU, the electronic display device being configured to display to a user information related to transferring data from analyte meters to the kiosk and options available for selection by the user, said data including a determination of analytes in body fluids for diagnosis and maintenance of the one or more physiological abnormalities, said determination of analytes in body fluids including periodical receipt and processing of a fluid sample from the user;
 an electronic input device mounted to the housing and coupled to the CPU, the electronic input device being configured to receive entries from the user and generate electronic signals indicative thereof;
 a memory inside the unitary housing and coupled to the CPU, the memory being adapted to store a meter communications control and intelligent diabetes data interpretation (IDDI) system program;
 a plurality of cable ports coupled to the CPU, the cable ports connecting the CPU with the various distinct types of analyte testing meters; and
 a plurality of cables with associated connectors, each of the cables being coupled to the CPU by a respective one of the cable ports, each of the associated connectors connecting to meters corresponding to a respective one of the various distinct types of analyte testing meters,
 wherein the unitary housing forms a unitary system for the various distinct types of analyte testing meters, the unitary housing containing the CPU, the electronic display device, the electronic input device, the memory, the plurality of cable ports and the plurality of cables,
 wherein, responsive to the electronic display device receiving and the CPU processing an entry from the user identifying one of the types of analyte testing meters, the electronic display device displays to the user connection information for the user to connect an analyte testing meter of the identified analyte testing meter type to the respective port via the appropriate cable and associated connector, the connection information facilitating the downloading of the data via direct interaction between the user and the kiosk without requiring assistance from a health care professional, and
 wherein said CPU, responsive to said downloading, presents processed data of at least some of the data to the health care professional for synthesis and interpretation of clinical implications.

13. A method of operating a data collection kiosk for downloading and processing patient analyte data for diagnosing or managing of one or more physiological abnormalities, the method comprising:
 providing, to a user via a data collection kiosk with a processor device, an input device, and a display device, a plurality of ports configured to connect the processor device with multiple different meter types, each of the respective ports including a respective distinct cable, each respective distinct cable having an associated connector which connects to a respective one of said different meter types, the meter types all being configured to measure patient analyte data and transmit the patient analyte data to the processor device of the data collection kiosk via the cables, said patient analyte data including a determination of analytes in body fluids for diagnosis and maintenance of the one or more physiological abnormalities, said determination of analytes in body fluids including periodical receipt and processing of a fluid sample from the user, the data collection kiosk having a unitary housing containing the processor device, the input device, the display device, and the plurality of ports, the unitary housing forming a unitary system for the different meter types;
 displaying to the user, on a screen of the display device of the data collection kiosk, options available for selection by the user to operate the kiosk, the options facilitating the downloading of the patient analyte data via direct interaction between the user and the data collection kiosk without requiring assistance from a health care professional;
 responsive to an entry received by the input device, and processed by the processor device of the kiosk, from the user identifying one of the meter types, displaying to the user, on the screen of the display device, connection information detailing how to connect a meter of the identified meter type to the respective port via the respective distinct cable;
 displaying to the user, on the screen of the display device, distinct predefined instructions detailing how to transfer the patient analyte data from the identified meter type to the data collection kiosk;
 in response to said user fulfilling said predefined instructions, transferring said patient analyte data from the identified meter type to said data collection kiosk without any interaction required from the health care professional; and
 in response to said transfer of said patient analyte data, presenting processed data of at least some of the patient analyte data to the health care professional for synthesis and interpretation of clinical implications.

14. The method of claim 13, wherein each of the cables includes an associated distinct connector, the associated distinct connector being configured to connect to the meters corresponding to the respective one of the multiple different meter types.

15. The method of claim 13, wherein the data collection kiosk further includes a printer within the unitary housing, the processor device being coupled to the plurality of ports, and the input device comprising a display touch screen coupled to the processor device.

16. The method of claim 13, further comprising printing a selected report generated from the patient analyte data.

17. The method of claim 16, further comprising processing, via the processor device, the downloaded patient analyte data and generating an intelligent diabetes data interpretation (IDDI) report.

18. The method of claim 13, further comprising displaying, via the display device, selected information responsive to a user entry requesting the selected information.

19. The method of claim 13, further comprising displaying, via the display device, a prompt for the user to enter a type of meter to be attached.

20. The method of claim 13, wherein the multiple different meter types all measure a blood glucose level, and each respective meter corresponding to the respective one of the meter types is a blood glucose monitor.

21. The method of claim 13, wherein the multiple different meter types correspond to more than one brand of meter.

* * * * *